US005776925A

United States Patent [19]
Young et al.

[11] Patent Number: 5,776,925
[45] Date of Patent: Jul. 7, 1998

[54] METHODS FOR CANCER CHEMOSENSITIZATION

[75] Inventors: Stuart W. Young; Richard A. Miller, both of Portola Valley, Calif.

[73] Assignee: Pharmacyclics, Inc., Sunnyvale, Calif.

[21] Appl. No.: 591,318

[22] Filed: Jan. 25, 1996

[51] Int. Cl.$^6$ .................................................... A61K 31/40
[52] U.S. Cl. .......................... 514/185; 514/2; 514/6; 514/8; 514/28; 514/32; 514/43; 514/44; 514/81; 514/245; 514/386; 514/410; 514/517; 514/564; 514/567; 514/589; 514/590
[58] Field of Search ........................... 514/2, 6, 28, 43, 514/44, 81, 410

[56] References Cited

U.S. PATENT DOCUMENTS

| | | | |
|---|---|---|---|
| 4,935,498 | 6/1990 | Sessler et al. | 534/15 |
| 5,252,720 | 10/1993 | Sessler et al. | 534/11 |
| 5,258,453 | 11/1993 | Kopecek et al. | 525/54.1 |
| 5,457,183 | 10/1995 | Sessler et al. | 534/11 |

FOREIGN PATENT DOCUMENTS

| | | |
|---|---|---|
| WO 90.10633 | 9/1990 | WIPO . |
| 94/29316 | 12/1994 | WIPO . |
| 95/21845 | 8/1995 | WIPO . |
| 96/09315 | 3/1996 | WIPO . |
| WO 96/40253 | 12/1996 | WIPO . |

OTHER PUBLICATIONS

Diddens, H., "Role of multidrug resistance in photodynamic therapy," *Optical Methods for Tumor Treatment and Detection*, 1645:115–123, 1992.

Nahabedian, et al., "Combination Cytotoxic Chemotherapy With Cisplatin or Doxorubicin and Photodynamic Therapy in Murine Tumors, " *Journal of the National Cancer Institute*, 80:739–743,1988.

International Search Report, PCT/US97/00907, mailed Jun. 30,1997.

Baas, et al., "Enhancement of photodynamic therapy by mitomycin C: a preclinical and clinical study", *British Journal of Cancer*, 73(8): 945–951, Apr. 1996.

Sessler et al., "Synthesis and Crystal Structure of a Novel Tripyrrane–Containing Porphyrinogen–like Macrocylce", *J. Org. Chem.*, 52:4394–4397, 1987.

Sessler et al., "The Coordination Chemistry of Planar Pentadentate Porphyrin–Like Ligands", *Comm. Inorg. Chem.*, 7:333–350, 1988.

Sessler et al., "An Expanded Porphyrin: The Synthesis and Structure of a New Aromatic Pentadentate Ligand", *J. Am. Chem. Soc.*, 110:5586–5588, 1988.

Sessler et al., "A Water–Stable Gadolinium (III) Complex Derived from a New Pentadentate Expanded Porphyrin Ligand", *Inorg. Chem.*, 28:3390–3393, 1989.

Sessler et al., "Binding of Pyridine and Benzimidazole to a Cadmium Expanded Porphyrin: Solution and X–ray Structural Studies", *Inorg. Chem.*, 28:1333–1341, 1989.

Harriman et al., "Metallotexaphyrins: A New Family of Photosensitisers for Efficient Generation of Singlet Oxygen", *J. Chem. SOc., Chem. Commun.*, 314–316, 1989.

Sessler et al., "Expanded Porphyrins: The Synthesis and Metal Binding Properties of Novel Tripyrrane–Containing Macrocycles", *J. Coord. Chem.*, 18:99–104, 1988.

Sessler et al., "The Synthesis and Structure of a Novel 22 π–Electron Aromatic Pentadentate Macrocyclic Ligand: An Expanded Porphyrin", Toronto ACS Meeting, Jun. 1988. USA.

Sessler et al., "A Water–Stable Gadolinium (III) Complex Derived from a New Pentadentate Expanded Porphyrin Ligand", *Chem. Absts.*, 111:720, abstract No. 125716e, Oct. 2, 1989.

Stinson, "Unusual Porphyrin Analog Promises Many Applications", *Chemical and Engineering News*, pp. 26–27, Aug. 8, 1988.

Sessler et al., "Tripyrroledimethine–derived (Texaphyrin–type) Macrocycles: Potential Photosensitizers Which Absorb in the Far–red Spectral Region", *SPIE, Optical Methods for Tumor Treatment and Early Diagnosis: Mechanism and Technique*, 1426:318–329, 1991.

Sessler et al., "'Texaphyrin ': A Novel 22 π–Electron Aromatic Pentadentate Macrocyclic Ligand", *ACS meeting*, Los Angeles, Sep. 1988.

Sessler and Burrell, "Expanded Porphyrins," *Topics in Current Chemistry*, 161:180–273, 1991.

Sessler et al., "Synthesis and Structural Characterization of Lanthanide(III) Texaphyrins," *Inorganic Chemistry*, 32(14):3175–3187, 1993.

Sessler et al., "Preparation of Lanthanide (III) Texaphyrin Complexes and Their Applications to Magnetic Resonance Imaging and Photodynamic Therapy," *Abstracts of Papers*, Part 1, 204th ACS National Meeting, Aug. 23–28, 1992, Wahington, DC.

Sessler et al., "Synthesis and Applications of Schiff–Base Derived Expanded Porphyrins," *Abstracts of Papers*, 204th ACS National Meeting, Aug. 23–28, 1992, Washington, DC.

Sessler, Jonathan L., "Texas–Sized Molecule," *Discovery*, 13(1):44–49, 193.

Sessler et al., "Photodynamic Inactivation of Enveloped Viruses Using Sapphyrin, α 22 π–Electron Expanded Porphyrin: Possible Approaches to Prophylactic Blood Purification Protocols," *SPIE Photodynamic Therapy: Mechanisms II*. 1203:233–245, 1990.

Maiya et al., "Ground–and Excited–State Spectral and Redox Properties of Cadmium(II) Texaphyrin," *Journal of Physical Chemistry*, 93(24):8111–8115, 1989.

(List continued on next page.)

*Primary Examiner*—Richard L. Raymond
*Attorney, Agent, or Firm*—Akin, Gump, Strauss, Hauer & Feld, L.L.P.

[57] ABSTRACT

Methods for cancer chemosensitization are provided. Texaphyrins are new chemosensitizers for enhancing the cytotoxicity of chemotherapeutic agents. The enhancement appears to be P-glycoprotein-independent since texaphyrins are effective in both a P-glycoprotein-expressing and a P-glycoprotein -nonexpressing cell line. Methods are provided for the treatment of cancers such as leukemia, lymphoma, carcinoma, and sarcoma using a texaphyrin as a chemosensitizer.

34 Claims, 1 Drawing Sheet

OTHER PUBLICATIONS

Sessler et al., "Texaphyrins: Synthesis and Applications," *Accounts of Chemical Research*, 27(2):43–50, 1994.

Leff, "Texas 'Son–of–Porphyrin' Molecule Lassos Europium to Kill Drug Resistence Gene," *BioWorld Today*, 5(156):1,1994.

Young et al., "Preclinical Evaluation of Gadolium (III) Texaphyrin Complex. A New Paramagnetic Contrast Agent for Magnetic Resonance Imaging," *Investigative Radiology*, 29(3):330–338, 1994.

Furuta et al., "Enhanced Transport of Nucleosides and Nucleoside Analogues with Complementary Base–Pairing Agents," *Journal of the American Chemical Society*, 113:4706–4707, 1991.

Sessler et al., "Anion Binding: A New Direction In Porphyrin–Related Research," *Pure & Applied Chem.*, 65(3):393–398, 1993.

Sessler et al., "Synthesis and Binding Properties of Monomeric and Dimeric Guanine and Cytosine Amine Derivatives," *J. Org. Chem.*, 1992, 57:818–826.

T.D. Mody et al., "Lutetium (III) Texaphyrin: A Novel Photodynamic Therapy Agent," Abstract, *22nd Annual American Society for Photobiology*, Scottsdale, AZ, Jun. 25–29, 1994.

Sessler et al., "Gadolilium (III) Texaphyrin: A Novel MRI Contrast Agent," *Journal of the American Chemical Society*, 115(22):10368–10369, 1993.

Iverson et al., "Interactions Between Porphyrins and Nucleic Acids," *Pure Applied Chemistry*, 66(4):845–850, 1994.

Magda et al., "Site–Specific Hydrolysis of RNA by Europium (III) Texaphyrin Conjugated to a Synthetic Oligodeoxyribonucleotide," *Journal of the American Chemical Society*, 116(16):7439–7440, 1994.

Koenig et al., "PDT of Tumor–Bearing Mice Using Liposome Delivered Texaphyrins," International Conference, Milan, Italy, Biosis citation only, Jun. 24–27, 1992.

Phillips and Wasserman, "Promise of Radiosensitizers and Radioprotectors in the Treatment of Human Cancer," *Cancer Treatment Reports*, 68(1):291–301, 1984.

Wagener and Beyrich, "Radiosensitizer–Biochemie und Tumortherapeutische Erfahrungen," *Pharmazie*, 47:815–824, 1992.

Magda et al., "Sequence–Specific Photocleavage of DNA by an Expanded Porphyrin with Irradiaton Above 700 nm," *J. Am. Chem. Soc.*, 117:3629–3630, 1995.

Sessler et al., "Expanded Porphyrins. Receptors for Cationic, Anionic, and Neutral Substrates," in Transition Metals in Supramolecular Chemistry, L. Fabbrizzi and A. Poggi, Editors, NATO ASI Series, Kluwer, Amsterdam, pp. 391–408, 1994.

PCT Search Report mailed Feb. 23, 1995 (PCT/US94/11491).

International Search Report mailed Dec. 6, 1994 (PCT/US94/06284).

International Search Report mailed Feb. 22, 1994 (PCT/US93/09994).

International Search Report mailed Feb. 3, 1994 (PCT/US93/09994).

Di Marco, et al., "–ivity of Adriamycin (NSC–123127 and Daunomycin (NSC–82151) –ainst Mouse Mammary Carcinoma", *Cancer Chemotherapy Reports*, Part 1 vol. 56, No. 2, Apr. 1972.

Di Marco, et al., "–oxic, Antiviral, and Antitumor Activity of Some Derivatives of –omycin (NSC 82151)", *Cancer Chemotherapy Reports*, Part 1 vol. 57, No. 3, Sep./Oct. 1973.

[edited by] DeVita, et al. *Cancer:Principles & Practice of Oncology*; 4th Edition; published by J.B. Lippincott Company, Philadelphia, pp. 2661–2666 and p. 19 of the index, 1993.

Casazza, A.M., "Antitumor Activity of Anthracyclines: Experimental Studies", pp. 13–29, *Anthracycline Antibiotics in Cancer Therapy*, [edited by] Muggia, et al., Proceedings of the International Symposium on Anthracycline Antibiotics in Cancer Therapy, New York, New York, 16–18 Sept. 1981, 1982.

Dorr and Von Hoff, *Cancer Chemotherapy Handbook*, 2nd Edition, Appleton & Lange, Norwalk, Connecticut, pp. 395–416, circa 1991.

Dorr and Von Hoff, *Cancer Chemotherapy Handbook*, 2nd Edition, Appleton & Lange, Norwalk, Connecticut, pp. 319–332, circa 1991.

[Edited by] Fidler and White, *Design of Models for Testing Cancer Therapeutic Agents*, Van Nostrand Reinhold Company, p. 104, 1982.

Grandi, et al., "Screening of Anthracycline Analogs", Bioactive Molecules vol. 4 Anthracycline and Anthracenedione–Based Anticancer Agents, [edited by] J.W. Lown, Elsevier, pp. 571–583, 1988.

*Physician's Desk Reference®*, 48th ed. Medical Economics, pub. 1994, pp. 458–461.

*Physician's Desk Reference®*, 48th ed. Medical Economics, pub. 1994, pp. 653–654.

*Physician's Desk Reference®*, 48th ed. Medical Economics, pub. 1994, pp. 655–657.

*Physician's Desk Reference®*, 48th ed. Medical Economics, pub. 1994, pp. 465–467.

*Physician's Desk Reference®*, 48th ed. Medical Economic, pub. 1994, pp. 666–670.

Rosenberg, B., Chapter 2 "Cisplatin: Its History and Possible Mechanisms of Action", *Cisplastin: Current Status and New Developments*, [edited by] Prestayko, et al., Academic Press, pp. 9–20, 1980.

Siemann and Mulcahy, "Sensitization of Cancer Chemotherapeutic Agents by Nitrohetercyclics", pp. 111–115, 1996.

Stubbe abd Kozarich, "Mechanisms of Bleomycin–Induced DNA Degradation", *Chemical Reviews* 87: 1107–1136, 1987.

Dialog Search in Patient Databases for Chemosensitization, Jan. 1996.

Dialog Search in Literature Databases for Chemosensitization, Jan. 1996.

PCT/US90/01208 Int'l Search Report mailed Aug. 2, 1990.

PCT/US95/12312 International Search Report mailed Feb. 9, 1996.

König et al., "PDT of Tumor–Bearing Mice Using Liposome Delivered Texaphyrins", International Conference on Photodynamic Therapy and Medical Laser Applications, Milan, Italy, Photodynamic Therapy and Biomedical Lasers, ed. Spinelli et al., Elsevier Science Publishers B.V., pp. 802–805, 1992.

König et al. "Photodynamic Activity of Liposome–Delivered Cd–Texaphyrin Using Tumor–Bearing Nude Mice", *Lasers in Surgery and Medicine* 13:522–527, 1993.

Iverson et al., "Interactions Between Expanded Porphyrins and Nucleic Acids" *Pure & Appl. Chem.*, vol. 66, No. 4, pp. 845–850, 1994.

METHODS FOR CANCER CHEMOSENSITIZATION

FIELD OF THE INVENTION

The present invention relates generally to the field of oncology, and to methods for enhancing the activity of a cancer chemotherapeutic agent. More particularly, it concerns the use of texaphyrin as a chemosensitizer for enhancing the cytotoxicity of a chemotherapeutic agent. Methods are provided for the treatment of cancers such as leukemia, lymphoma, carcinoma, and sarcoma using a texaphyrin as a chemosensitizer.

BACKGROUND OF THE INVENTION

Many of the most prevalent forms of human cancer resist effective chemotherapeutic intervention. Some tumor populations, especially adrenal, colon, jejunal, kidney and liver carcinomas, appear to have drug-resistant cells at the outset of treatment (Barrows, L. R., 1995). In other cases, resistance appears to be acquired in much the same way as microbial resistance, a resistance-conferring genetic change occurs during treatment; the resistant daughter cells then proliferate in the environment of the drug. Whatever the cause, resistance often terminates the usefulness of an antineoplastic drug.

Clinical studies suggest that a common form of multidrug resistance in human cancers results from the expression of the MDR1 gene that encodes P-glycoprotein. This glycoprotein functions as a plasma membrane, energy-dependent, multidrug efflux pump that reduces the intracellular concentration of cytotoxic drugs. This mechanism of resistance may account for de novo resistance in common tumors, such as colon cancer and renal cancer, and for acquired resistance, as observed in common hematologic tumors such as acute nonlymphocytic leukemia and malignant lymphomas. Although this type of drug resistance may be common, it is by no means the only mechanism by which cells become drug resistant.

Chemical modification of cancer treatment involves the use of agents or maneuvers that are not cytotoxic in themselves, but modify the host or tumor so as to enhance anticancer therapy. Such agents are called chemosensitizers. Pilot studies using chemosensitizers indicate that these agents may reverse resistance in a subset of patients. These same preliminary studies also indicate that drug resistance is multifactorial, because not all drug-resistant patients have P-glycoprotein-positive tumor cells and only a few patients appear to benefit from the use of current chemosensitizers.

Chemosensitization research has centered on agents that reverse or modulate multidrug resistance in solid tumors (MDR1, P-glycoprotein). Chemosensitizers known to modulate P-glycoprotein function include: calcium channel blockers (verapamil), calmodulin inhibitors (trifluoperazine), indole alkaloids (reserpine), quinolines (quinine), lysosomotropic agents (chloroquine), steroids, (progesterone), triparanol analogs (tamoxifen), detergents (cremophor EL), and cyclic peptide antibiotics (cyclosporines) (De Vita, 1993).

A review of studies where chemosensitizing agents were used concluded the following: i) cardiovascular side effects associated with continuous, high-dose intravenous verapamil therapy are significant and dose-limiting, ii) dose-limiting toxicities of the chemosensitizers, trifluoperazine and tamoxifen, was attributed to the inherent toxicity of the chemosensitizer and not due to enhanced chemotherapy toxicity, iii) studies using high doses of cyclosporin A as a chemosensitizer found hyperbilirubinemia as a side effect, and iv) further research is clearly needed to develop less toxic and more efficacious chemosensitizers to be used clinically (DeVita et al., 1993).

Tumors that are considered drug-sensitive at diagnosis but acquire an MDR phenotype at relapse pose an especially difficult clinical problem. At diagnosis, only a minority of tumor cells may express P-glycoprotein and treatment with chemotherapy provides a selection advantage for the few cells that are P-glycoprotein positive early in the course of disease. Another possibility is that natural-product-derived chemotherapy actually induces the expression of MDR1, leading to P-glycoprotein-positive tumors at relapse. Using chemosensitizers early in the course of disease may prevent the emergence of MDR by eliminating the few cells that are P-glycoprotein positive at the beginning. In vitro studies have shown that selection of drug-resistant cells by combining verapamil and doxorubicin does prevent the emergence of P-glycoprotein, but that an alternative drug resistance mechanism develops, which is secondary to altered topoisomerase II function (Dalton, W. S., 1990).

Several reasons may explain the failure of current chemosensitizers to reverse clinical multidrug resistance: i) levels of the chemosensitizing agent may be inadequate at the tumor site, ii) levels of P-glycoprotein may increase as the tumor progresses, iii) the MDR1 gene may mutate, resulting in decreased binding of the chemosensitizing agent to P-glycoprotein, iv) alternative non-P-glycoprotein mechanisms of resistance may emerge during treatment that are unaffected by chemosensitizers, and v) chemosensitizers have lacked tumor selectivity and have sensitized normal tissues to the toxic effects of chemotherapy. One non-P-glycoprotein mechanism is due to altered topoisomerase II function that may confer resistance to anthracycline and epipodophyllotoxins (DeVita et al., 1993).

More efficacious and less toxic chemosensitizers are urgently needed to improve the outcome of chemotherapy. Clinical utility of a chemosensitizer depends upon its ability to enhance the cytotoxicity of a chemotherapeutic drug and also on its low toxicity in vivo. The present inventors have addressed these problems and provide herein a new class of chemosensitizers that permit new approaches in cancer treatment.

SUMMARY OF THE INVENTION

The present invention provides a method of chemosensitization comprising administering a chemotherapeutic agent and a texaphyrin to a subject. "Chemosensitization", as used herein, means that a texaphyrin increases or enhances the cytotoxicity of a chemotherapeutic agent compared to a level of cytotoxicity seen by that agent in the absence of texaphyrin. That is, texaphyrin "sensitizes" a cancer cell to the effects of the chemotherapeutic agent, allowing the agent to be more effective. Texaphyrin is not known to have anti-cancer chemotherapeutic activity on its own.

An embodiment of the present invention is a method of treating cancer in a subject comprising administering a chemotherapeutic agent and a texaphyrin to the subject. The cancer may be leukemia, lymphoma, carcinoma, or sarcoma. In a preferred embodiment, a patient having a form of cancer for which chemotherapy is indicated is administered a dose of texaphyrin at intervals with each dose of the chemotherapeutic agent.

Chemosensitization may be combined with photodynamic therapy applications since texaphyrin is a photosensitive molecule and has absorption in the physiologically important range of 700–900 nm (see the U.S. Patents to texaphyrins cited herein, incorporated herein by reference for this purpose). The method is that of treating a cancer comprising administering a chemotherapeutic agent and a photosensitive texaphyrin to a patient, and irradiating the patient in the vicinity of the cancer. In this combined treatment, the texaphyrin may be metal-free or in a complex with a metal. If metallated, the metal is a diamagnetic metal cation and the diamagnetic metal cation may be Lu(III), La(III), In(III), Y(III), Zn(II) or Cd(II), preferably the metal cation is Lu(III).

Imaging may be combined with chemosensitization since gadolinium texaphyrin is an excellent contrast agent for magnetic resonance imaging (see the U.S. Patents to texaphyrins cited herein, incorporated herein by reference for this purpose). The method is that of treating a cancer comprising administering a chemotherapeutic agent and a paramagnetic metal-texaphyrin complex to a patient, and imaging the patient. This technique treats the cancer with the chemotherapeutic agent having enhanced activity in the presence of texaphyrin, and allows for the monitoring of the location and size of a tumor, for example. The paramagnetic metal cation may be Mn(II), Mn(III), Fe(III), or trivalent lanthanide metal cations other than La(III), Lu(III), and Pm(III). More preferably, the paramagnetic metal is Mn(II), Mn(III), Dy(III), or Gd(III); and most preferably, Dy(III) or Gd(III).

The present invention further provides a method of treating cancer in a subject including the steps of administering to the subject a chemotherapeutic agent and a texaphyrin having radiosensitization properties, and administering ionizing radiation to the subject in proximity to the cancer. Texaphyrins have been demonstrated to have radiation sensitization properties; they enhance cytotoxicity from ionizing radiation in the vicinity of the texaphyrin as compared to control experiments (see PCT publication WO 95/10307, incorporated by reference herein). Ionizing radiation includes, but is not limited to, x-rays, internal and external gamma emitting radioisotopes, and ionizing particles. In this combined treatment, the texaphyrin may be complexed with a metal, although the metal is not central to the radiosensitization properties of the texaphyrins.

In another aspect of the invention, texaphyrins may be used as a topical chemosensitizer. Table 2 indicates that 5-fluorouracil, for example, is used topically for premalignant skin lesions. The inventors envision the use of texaphyrins to enhance the cytotoxicity of topical chemotherapeutic agents.

A method for selecting a chemotherapeutic agent for which texaphyrin is a chemosensitizer is a further embodiment of the present invention. The method comprises the steps of i) assaying cytotoxicity of a candidate chemotherapeutic agent in the presence and in the absence of texaphyrin, and ii) selecting a candidate chemotherapeutic agent as a chemotherapeutic agent for which texaphyrin is a chemosensitizer when the cytotoxicity of the candidate agent is greater in the presence of texaphyrin than in the absence of texaphyrin. A presently preferred in vitro assay is the MTT cytotoxicity assay cited in example 1; an exemplary in vivo assay is described in example 2.

Following long-standing patent law convention, the terms "a" and "an" mean "one or more" when used in this application, including the claims.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE PREFERRED EMBODIMENTS

Figure 1:
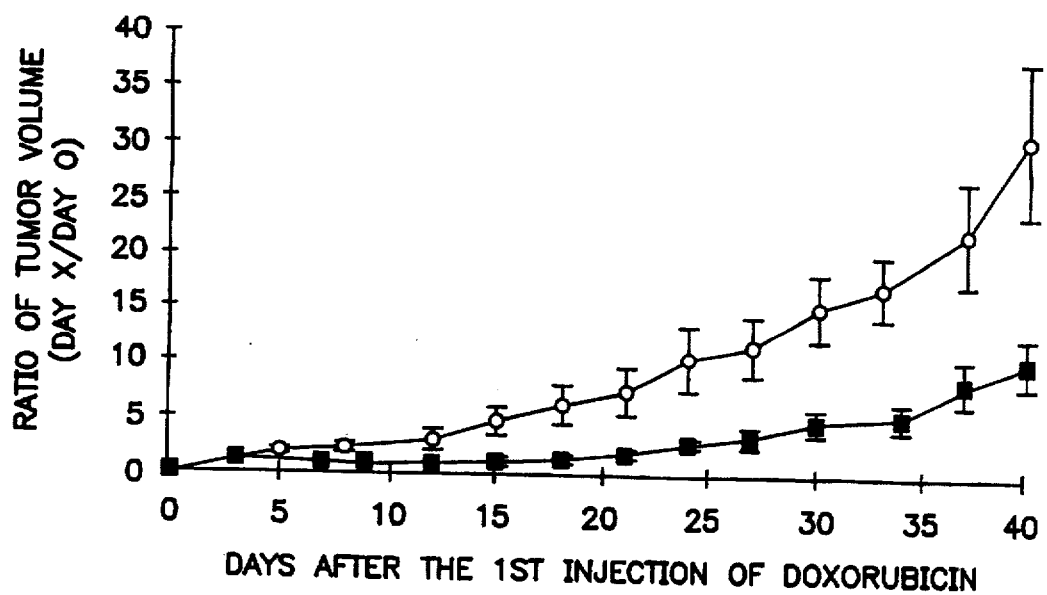
FIG. 1 provides a standard error analysis of data obtained from injecting doxorubicin only (○) and injecting doxorubicin followed by texaphyrin 5 min and 5 hr later (■). Error bars represent standard error, n=14.

The present invention results from the discovery that texaphyrins are chemosensitizers. Chemosensitization using a texaphyrin refers to an enhancement of cytotoxicity on the part of a chemotherapeutic agent when that agent is administered in conjunction with administering a texaphyrin.

The chemotherapeutic agent may be one of the following: an alkylating agent such as a nitrogen mustard, an ethylenimine and a methylmelamine, an alkyl sulfonate, a nitrosourea, and a triazene; an antimetabolite such as a folic acid analog, a pyrimidine analog, and a purine analog; a natural product such as a vinca alkaloid, an epipodophyllotoxin, an antibiotic, an enzyme, a taxane, and a biological response modifier; miscellaneous agents such as a platinum coordination complex, an anthracenedione, an anthracycline, a substituted urea, a methyl hydrazine derivative, or an adrenocortical suppressant; or a hormone or an antagonist such as an adrenocorticosteroid, a progestin, an estrogen, an antiestrogen, an androgen, an antiandrogen, or a gonadotropin-releasing hormone analog. Specific examples of alkylating agents, antimetabolites, natural products, miscellaneous agents, hormones and antagonists, and the types of cancer for which these classes of chemotherapeutic agents are indicated are provided in Table 2. Preferably, the chemotherapeutic agent is a nitrogen mustard, an epipodophyllotoxin, an antibiotic, or a platinum coordination complex. A more preferred chemotherapeutic agent is bleomycin, doxorubicin, paclitaxel, etoposide, 4-OH cyclophosphamide, or cisplatinum. A presently preferred chemotherapeutic agent is doxorubicin or bleomycin.

Texaphyrin compounds, methods for making and methods for using them are described in U.S. Pat. Nos. 4,935,498, 5,162,509, 5,252,720, 5,272,142, 5,256,399, 5,292,414, 5,432,171, 5,439,570, 5,475,104, 5,451,576, 5,457,183, and 5,369,101; in pending applications U.S. application Ser. Nos. 08/098,514 (since issued as U.S. Pat. No. 5,569,759), 08/196,964 (since issued as U.S. Pat. No. 5,599,923), 08/227,370 (since issued as U.S. Pat. No. 5,559,207), 08/207,845 (since issued as U.S. Pat. No. 5,587,463), 08/236,218 (since abandoned), and 08/484,551, and in PCT publications WO 90/10633, WO 93/14093, and WO 94/29316; each patent, application, and publication is incorporated by reference herein.

The use of texaphyrin as a chemosensitizer has an important added advantage due to the inherent biolocalization of texaphyrin. "Inherent biolocalization" means having a selectively greater affinity for certain tissues relative to surrounding tissues. As described in the '720 patent, texaphyrins localize in lipid-rich regions such as, for example, liver, kidney, tumor and atheroma. This biolocalization would enhance cytoxicity in those areas and not in normal tissues. It may thus be possible to administer less chemotherapeutic agent in the presence of texaphyrin to obtain a desired effect. As a result of being exposed to less chemotherapy, the patient may experience less general toxicity, while lipid-rich regions such as tumors experience enhanced cytotoxicity.

Furthermore, a texaphyrin may be coupled to a site-directing molecule to form a conjugate for targeted in vivo delivery. "Site-directing" means having specificity for targeted sites. "Specificity for targeted sites" means that upon contacting the texaphyrin-site-directing-conjugate with the targeted site, for example, under physiological conditions of ionic strength, temperature, PH and the like, specific binding will occur. The interaction may occur due to specific electrostatic, hydrophobic, entropic or other interaction of certain residues of the conjugate with specific residues of the target to form a stable complex under conditions effective to promote the interaction. Exemplary site-directing molecules contemplated in the present invention include but are not limited to: oligonucleotides, polyamides including peptides having affinity for a biological receptor and proteins such as antibodies; steroids and steroid derivatives; hormones such as estradiol, or histamine; hormone mimics such as morphine; and further macrocycles such as sapphyrins and rubyrins.

The mechanism of action of texaphyrins as chemosensitizers is not known; while not wanting to be bound by theory, it is possible that texaphyrins may inhibit repair of cellular damage caused by the chemotherapeutic agent, texaphyrins may compromise the cell's energy stores or may increase free radical life span. Since the action as a chemosensitizer appears to be P-glycoprotein-independent (see Example 9), a unique P-glycoprotein-independent mechanism appears to be occurring. A "P-glycoprotein-independent chemosensitizer" as used herein means that texaphyrins are effective as a chemosensitizer independent of the MDR1 mechanism of resistance that may be induced in a cancer cell. The fact that texaphyrins are effective as chemosensitizers in both an MDR-expressing and an MDR-nonexpressing cell line sets the texaphyrins apart from current chemosensitizers that are targeted to address the MDR mechanism of resistance.

Texaphyrins used as chemosensitizers may be administered before together with or after administration of the chemotherapeutic agent. Administration of the texaphyrin after the chemotherapeutic agent is presently preferred. The texaphyrin may be administered as a single dose, or it may be administered as two or more doses separated by an interval of time. The texaphyrin may be administered from about one minute to about 12 hr following administration of the chemotherapy agent, preferably from about 5 min to about 5 hr. Where the texaphyrin is administered as two or more doses, the time interval between the texaphyrin administrations may be from about one minute to about 12 hr, preferably from about 5 min to about 5 hr, more preferably about 4 to 5 hr. The dosing protocol may be repeated; from one to three times, for example. A time frame that has been successful in vivo is administration of texaphyrin about 5 min and about 5 hr after administration of the chemotherapeutic agent, with the protocol being performed once per week for three weeks. A dose of about 40 μmol/kg texaphyrin was used. Administration may be intravenous, intraperitoneal, parenteral, intramuscular, subcutaneous, oral, or topical, with topical and intravenous administration being preferred, and intravenous being more preferred.

The texaphyrin to be used in the method of the invention will be administered in a pharmaceutically effective amount. By "pharmaceutically effective" is meant that dose which will provide an enhanced toxicity to a chemotherapeutic agent. The specific dose will vary depending on the particular texaphyrin chosen, the dosing regimen to be followed, and the particular chemotherapeutic agent with which it is administered. Such dose can be determined without undue experimentation by methods known in the art or as described herein.

One of skill in the art in light of the present disclosure would realize flexibility in the above regimen and would be able to test, without undue experimentation, for optimal timing and dosage for administration of a texaphyrin for a particular circumstance.

A texaphyrin for use as a chemosensitizer may have structure I:

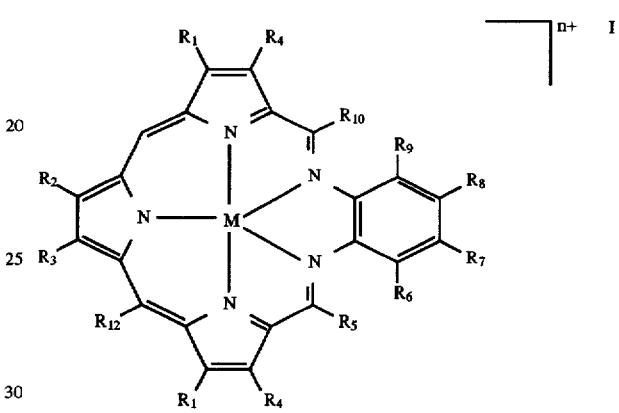

In this embodiment, M is H, a divalent metal cation, or a trivalent metal cation. A preferred divalent metal cation is Ca(II), Mn(II), Co(II), Ni (II), Zn(II), Cd(II), Hg(II), Fe(II), Sm(II), or $UO_2$ (II). A preferred trivalent metal cation is Dy(III), Er(III), Tm(III), Yb(III), Lu(III), La(III), or U(III).

$R_1$–$R_4$, $R_7$ and $R_8$ are independently hydrogen, halide, hydroxyl, alkyl, aryl, haloalkyl, nitro, formyl, acyl, hydroxyalkyl, alkoxy, hydroxyalkoxy, saccharide, carboxy, carboxyalkyl, carboxyamidealkyl, a site-directing molecule, or a couple that is coupled to a site-directing molecule.

$R_6$ and $R_9$ are independently selected from the groups of $R_1$–$R_4$, $R_7$ and $R_8$, with the proviso that the halide is other than iodide and the haloalkyl is other than iodoalkyl.

$R_5$ and $R_{10}$–$R_{12}$ are independently hydrogen, alkyl, aryl, hydroxyalkyl, alkoxy, hydroxyalkoxy, carboxyalkyl, carboxyamidealkyl or a couple that is coupled to a saccharide or to a site-directing molecule; and n is an integer less than or equal to 5.

The term "n" will typically be an integer less than or equal to 5. In the context of the basic macrocycle with a divalent or trivalent metal cation, n is 1 or 2; however, one skilled in the art in light of the present disclosure would realize that the value of n would be altered due to charges present on substituents $R_1$–$R_{12}$, for example, charges present on a covalently bound site-directing molecule. Complexes described in the present invention have one or more additional ligands providing charge neutralization and/or coordinative saturation to the metal ion. Such ligands include chloride, nitrate, acetate, and hydroxide, among others.

In a nonmetallated form of texaphyrin, an alkyl group may be attached to a ring nitrogen. A texaphyrin having a methyl group attached to a ring nitrogen is described in U.S. Pat. No. 5,457,183, incorporated by reference herein.

As used herein, a "site-directing molecule" may be an oligonucleotide, an antibody, a hormone, a peptide having affinity for a biological receptor, a sapphyrin molecule, and the like. A preferred site-directing molecule is a hormone, such as estradiol, estrogen, progesterone, and the like. A site-directing molecule may have binding specificity for localization to a treatment site and a biological receptor may be localized to a treatment site. A texaphyrin oligonucleotide-conjugate, where the oligonucleotide is complementary to an oncogenic messenger RNA, for example, would further localize chemotherapeutic activity to a particularly desired site. Antisense technology is discussed in U.S. Pat. Nos. 5,194,428, 5,110,802 and 5,216,141, all of which are incorporated by reference herein.

A couple may be described as a linker, i.e., the covalent product formed by reaction of a reactive group designed to attach covalently another molecule at a distance from the texaphyrin macrocycle. Exemplary linkers or couples are amides, amine, thiol, thioether, ether, or phosphate covalent bonds. In most preferred embodiments, site-directing molecules are covalently bonded to the texaphyrin via a carbon-nitrogen, carbon-sulfur, or a carbon-oxygen bond.

The following structure shows a correlation of the IUPAC nomenclature for the positions of the atoms around the periphery of the macrocycle with the positions of the R groups of the present invention.

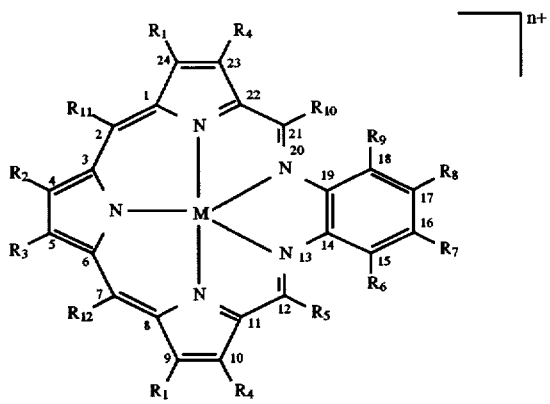

Substituents at the $R_6$ and $R_9$ positions on the B (benzene ring) portion of the macrocycle are incorporated into the macrocycle by their attachment to ortho-phenylenediamine in the 3 and 6 positions of the molecule. Substituents at the $R_5$ and $R_{10}$ positions on the T (tripyrrane) portion of the macrocycle are incorporated by appropriate functionalization of carboxyl groups in the 5 positions of the tripyrrane at a synthetic step prior to condensation with a substituted ortho-phenylenediamine.

Generally, water soluble texaphyrins retaining lipophilicity are preferred for the applications described herein. "Water soluble" means soluble in aqueous fluids to about 1 mM or better. "Retaining lipophilicity" means having greater affinity for lipid rich tissues or materials than surrounding nonlipid rich tissues. "Lipid rich" means having a greater amount of triglyceride, cholesterol, fatty acids or the like.

In the texaphyrins of the present invention, the alkyl, aryl, hydroxyalkyl, oxyalkyl, oxyhydroxyalkyl, saccharide, carboxyalkyl, carboxyamidealkyl, site-directing molecule, or molecule couple is covalently bonded to the texaphyrin via a carbon-carbon, a carbon-nitrogen or a carbon-oxygen bond.

The aryl may be a compound whose molecules have the ring structure characteristic of benzene, naphthalene, phenanthrene, anthracene, and the like, i.e., either the 6-carbon ring of benzene or the condensed 6-carbon rings of the other aromatic derivatives. For example, an aryl group may be phenyl or naphthyl, unsubstituted or substituted with a nitro, carboxy, sulfonic acid, hydroxy, oxyalkyl or halide substituent. In this case, the substituent on the phenyl or naphthyl may be added in a synthetic step after the condensation step which forms the macrocycle.

Representative examples of alkanes useful as alkyl group substituents of the present invention include methane, ethane, straight-chain, branched or cyclic isomers of propane, butane, pentane, hexane, heptane, octane, nonane and decane, with methane, ethane and propane being preferred. Representative examples of alkenes useful as alkenyl group substituents include ethene, straight-chain, branched or cyclic isomers of propene, butene, pentene, hexene, heptene, octene, nonene and decene, with ethene and propene being preferred. Representative examples of alkynes useful as alkynyl group substituents include ethyne, straight-chain, branched or cyclic isomers of propyne, butyne, pentyne, hexyne, heptyne, octyne, nonyne and decyne, with ethyne and propyne being preferred. Representative examples of substituted alkyls include alkyls substituted by two or more functional groups as described herein.

Among the halide substituents, chloride, bromide, fluoride and iodide are contemplated in the practice of this invention with the exception of iodide for $R_6$ and $R_9$. $R_6$ and $R_9$ may have chloride, bromide or fluoride substituents. Representative examples of haloalkyls used in this invention include halides of methane, ethane, propane, butane, pentane, hexane, heptane, octane, nonane and decane, with halides, preferably chlorides or bromides, of methane, ethane and propane being preferred.

Representative examples of hydroxyalkyls include alcohols of methane, ethane, straight-chain, branched or cyclic isomers of propane, butane, pentane, hexane, heptane, octane, nonane and decane, with alcohols of methane, ethane or propane being preferred. "Hydroxyalkyl" is meant to include glycols and polyglycols; diols of ethane, straight-chain, branched or cyclic isomers of propane, butane, pentane, hexane, heptane, octane, nonane and decane, with diols of ethane or propane being preferred; polyethylene glycol, polypropylene glycol and polybutylene glycol as well as polyalkylene glycols containing combinations of ethylene, propylene and butylene.

Representative examples of oxyalkyls include the alkyl groups as herein described having ether linkages. The number of repeating oxyalkyls within a substituent may be up to 100, preferably is from 1–10, and more preferably, is 2–5. A preferred oxyalkyl is $O(CH_2CH_2O)_xCH_3$ where x=1–100, preferably 1–10, and more preferably, 2–5.

Representative examples of thioalkyls include thiols of -ethane, thiols of straight-chain, branched or cyclic isomers of propane, butane, pentane, hexane, heptane, octane, nonane and decane, with thiols of ethane (ethanethiol, $C_2H_5SH$) or propane (propanethiol, $C_3H_7SH$) being preferred. Sulfate-substituted alkyls include alkyls as described above substituted by one or more sulfate groups, a representative example of which is diethyl sulfate ($(C_2H_5)_2SO_4$).

Representative examples of phosphates include phosphate or polyphosphate groups. Representative examples of phosphate-substituted alkyls include alkyls as described above substituted by one or more phosphate or polyphosphate groups. Representative examples of phosphonate-substituted alkyls include alkyls as described above substituted by one or more phosphonate groups.

Representative examples of carboxy groups include carboxylic acids of the alkyls described above as well as aryl carboxylic acids such as benzoic acid. Representative examples of carboxyamides include primary carboxyamides ($CONH_2$), secondary (CONHR') and tertiary (CONR'R") carboxyamides where each of R' and R" is a functional group as described herein.

Representative examples of useful amines include a primary, secondary or tertiary amine of an alkyl as described hereinabove.

Representative examples of useful steroids include any of the steroid hormones of the following five categories: progestins (e.g. progesterone), glucocorticoids (e.g., cortisol), mineralocorticoids (e.g., aldosterone), androgens (e.g., testosterone) and estrogens (e.g., estradiol).

Representative examples of useful amino acids of peptides or polypeptides include amino acids with simple aliphatic side chains (e.g., glycine, alanine, valine, leucine, and isoleucine), amino acids with aromatic side chains (e.g., phenylalanine, tryptophan, tyrosine, and histidine), amino acids with oxygen and sulfur-containing side chains (e.g., serine, threonine, methionine, and cysteine), amino acids with side chains containing carboxylic acid or amide groups (e.g., aspartic acid, glutamic acid, asparagine, and glutamine), and amino acids with side chains containing strongly basic groups (e.g., lysine and arginine), and proline. Representative examples of useful peptides include any of both naturally occurring and synthetic di-, tri-, tetra-, pentapeptides or longer peptides derived from any of the above described amino acids (e.g., endorphin, enkephalin, epidermal growth factor, poly-L-lysine, or a hormone). Representative examples of useful polypeptides include both naturally occurring and synthetic polypeptides (e.g., insulin, ribonuclease, and endorphins) derived from the above described amino acids and peptides.

Hydroxyalkyl means alkyl groups having hydroxyl groups attached. Oxyalkyl means alkyl groups attached to an oxygen. Oxyhydroxyalkyl means alkyl groups having ether or ester linkages, hydroxyl groups, substituted hydroxyl groups, carboxyl groups, substituted carboxyl groups or the like. Saccharide includes oxidized, reduced or substituted saccharide; hexoses such as D-glucose, D-mannose or D-galactose; pentoses such as D-ribulose or D-fructose; disaccharides such as sucrose, lactose, or maltose; derivatives such as acetals, amines, and phosphorylated sugars; oligosaccharides, as well as open chain forms of various sugars, and the like. Examples of amine-derivatized sugars are galactosamine, glucosamine, sialic acid and D-glucamine derivatives such as 1-amino-1-deoxysorbitol. Carboxyamidealkyl means alkyl groups with hydroxyl groups, secondary or tertiary amide linkages or the like. Carboxyalkyl means alkyl groups having hydroxyl groups, carboxyl or amide substituted ethers, ester linkages, tertiary amide linkages removed from the ether or the like.

The term "a peptide having affinity for a biological receptor" means that upon contacting the peptide with the biological receptor, for example, under appropriate conditions of ionic strength, temperature, pH and the like, specific binding will occur. The interaction may occur due to specific electrostatic, hydrophobic, entropic or other interaction of certain amino acid or glycolytic residues of the peptide with specific amino acid or glycolytic residues of the receptor to form a stable complex under the conditions effective to promote the interaction. The interaction may alter the three-dimensional conformation and the function or activity of either or both the peptide and the receptor involved in the interaction. A peptide having affinity for a biological receptor may include an endorphin, an enkephalin, a growth factor, e.g. epidermal growth factor, poly-L-lysine, a hormone, a peptide region of a protein and the like. A hormone may be estradiol, for example.

Preferred functionalizations are: when $R_6$ and $R_9$ are other than hydrogen, then $R_5$ and $R_{10}$ are hydrogen or methyl; and when $R_5$ and $R_{10}$ are other than hydrogen, then $R_6$ and $R_9$ are hydrogen, hydroxyl, or halide other than iodide. Other preferred functionalizations are where $R_6$ and $R_9$ are hydrogen, then $R_5$, $R_{10}$, $R_{11}$ and $R_{12}$ are independently hydrogen, phenyl, lower alkyl or lower hydroxyalkyl. The lower alkyl is preferably methyl or ethyl, more preferably methyl. The lower hydroxyalkyl is preferably of 1 to 6 carbons and 1 to 4 hydroxy groups, more preferably 3-hydroxypropyl. The phenyl may be substituted or unsubstituted.

In other presently preferred texaphyrin compounds I, $R_1$–$R_4$, $R_7$, and $R_8$ are as in Table 1 for texaphyrins A1–A22, $R_5$, $R_6$, and $R_9$–$R_{12}$ are H, and M is as defined hereinabove. Most preferred are the compounds GdT2BET (compound II where M=Gd(III)) and LuT2BET (compound II where M=Lu(III)). While the cited texaphyrins are presently preferred for use in the present invention, the invention is not limited thereto.

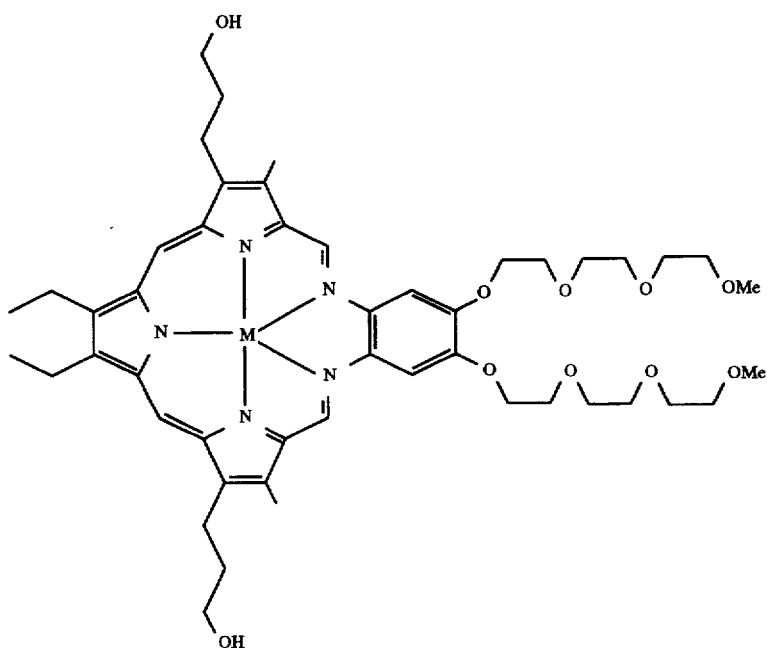

II

TABLE 1

Representative Substituents for
Texaphyrin Macrocycles of the Present Invention

| TXP | $R_1$ | $R_2$ | $R_3$ | $R_4$ | $R_8$ | $R_7$ |
|---|---|---|---|---|---|---|
| A1 | $CH_2(CH_2)_2OH$ | $CH_2CH_3$ | $CH_2CH_3$ | $CH_3$ | $O(CH_2)_3OH$ | $O(CH_2)_3OH$ |
| A2 | " | " | " | " | $O(CH_2CH_2O)_3CH_3$ | $O(CH_2CH_2O)_3CH_3$ |
| A3 | " | " | " | " | $O(CH_2)_n$CON-linker-site-directing molecule, n = 1-10 | " |
| A4 | " | " | " | " | $O(CH_2)_n$CON-linker-site-directing molecule, n = 1-10 | H |
| A5 | " | " | " | " | $OCH_2CO$-hormone | " |
| A6 | " | " | " | " | $O(CH_2CH_2O)_3CH_3$ | " |
| A7 | " | " | " | " | $OCH_2CON$-linker-site-directing molecule | $O(CH_2CH_2O)_3CH_3$ |
| A8 | " | " | " | " | $CH_2CO$-hormone | " |
| A9 | " | " | " | " | $O(CH_2CH_2O)_{120}CH_3$ | $O(CH_2CH_2O)_3CH_2$-$CH_2$-N-imidazole |
| A10 | " | " | " | " | saccharide | H |
| A11 | " | " | " | " | $OCH_2CON(CH_2CH_2OH)_2$ | " |
| A12 | " | " | " | " | $CH_2CON(CH_3)CH_2(CHOH)_4CH_2OH$ | " |
| A13 | " | COOH | COOH | " | $CH_2CON(CH_3)CH_2(CHOH)_4CH_2OH$ | " |
| A14 | " | $COOCH_2CH_3$ | $COOCH_2CH_3$ | " | $CH_2CON(CH_3)CH_2(CHOH)_4CH_2OH$ | " |
| A15 | $CH_2CH_2CON(CH_2CH_2OH)_2$ | $CH_2CH_3$ | $CH_2CH_3$ | " | $CH_2CON(CH_3)CH_2(CHOH)_4CH_2OH$ | " |
| A16 | $CH_2CH_2ON(CH_3)CH_2$-$(CHOH)_4CH_2OH$ | " | " | " | $OCH_3$ | $OCH_3$ |
| A17 | $CH_2(CH_2)_2OH$ | " | " | " | $O(CH_2)_n COOH$, n = 1-10 | H |
| A18 | " | " | " | " | $(CH_2)_n$-CON-linker-site-directing molecule, n = 1-10 | " |
| A19 | " | " | " | " | $YCOCH_2$-linker-site-directing molecule Y=NH, O | " |
| A20 | $CH_2CH_3$ | $CH_3$ | $CH_2CH_2COOH$ | " | $O(CH_2)_2CH_2OH$ | $O(CH_2)_2CH_2OH$ |

TABLE 1-continued

Representative Substituents for Texaphyrin Macrocycles of the Present Invention

| TXP | $R_1$ | $R_2$ | $R_3$ | $R_4$ | $R_8$ | $R_7$ |
|---|---|---|---|---|---|---|
| A21 | " | " | $CH_2CH_2CON$-oligo | " | " | " |
| A22 | $CH_2(CH_2)_2OH$ | $CH_2CH_3$ | $CH_2CH_3$ | " | $O(CH_2)_3CO$-histamine | H |

For use as a chemosensitizer, texaphyrins are provided as pharmaceutical preparations. A pharmaceutical preparation of a texaphyrin may be administered alone or in combination with pharmaceutically acceptable carriers, in either single or multiple doses. Suitable pharmaceutical carriers include inert solid diluents or fillers, sterile aqueous solution and various organic solvents. The pharmaceutical compositions formed by combining a texaphyrin of the present invention and the pharmaceutically acceptable carriers are then easily administered in a variety of dosage forms such as injectable solutions.

For parenteral administration, solutions of the texaphyrin in sesame or peanut oil, aqueous propylene glycol, or in sterile aqueous solution may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy use with a syringe exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars such as mannitol or dextrose or sodium chloride. A more preferable isotonic agent is a mannitol solution of about 2–8% concentration, and, most preferably, of about 5% concentration. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

The present inventors envision that texaphyrins may be used as chemosensitizers for enhancing the cytotoxicity of a variety of chemotherapeutic agents having differing mechanisms of action. A listing of currently available chemotherapeutic agents according to class, and including diseases for which the agents are indicated, is provided as Table 2.

TABLE 2

Chemotherapeutic Agents Useful in Neoplastic Disease[1]

| Class | Type of Agent | Name | Disease[2] |
|---|---|---|---|
| Alkylating Agents | Nitrogen Mustards | Mechlorethamine ($HN_2$) | Hodgkin's disease, non-Hodgkin's lymphomas |
| | | Cyclophosphamide Ifosfamide | Acute and chronic lymphocytic leukemias, Hodgkin's disease, non-Hodgkin's lymphomas, multiple myeloma, neuroblastoma, breast, ovary, lung, Wilms' tumor, cervix, testis, soft-tissue sarcomas |
| | | Melphalan | Multiple myeloma, breast, ovary |

TABLE 2-continued

Chemotherapeutic Agents Useful in Neoplastic Disease[1]

| Class | Type of Agent | Name | Disease[2] |
|---|---|---|---|
| | | Chlorambucil | Chronic lymphocytic leukemia, primary macroglobulinemia, Hodgkin's disease, non-Hodgkin's lymphomas |
| | | Estramustine | Prostate |
| | Ethylenimines and Methylmelamines | Hexamethyl-melamine | Ovary |
| | | Thiotepa | Bladder, breast, ovary |
| | Alkyl Sulfonates | Busulfan | Chronic granulocytic leukemia |
| | Nitrosoureas | Carmustine | Hodgkin's disease, non-Hodgkin's lymphomas, primary brain tumors, multiple myeloma, malignant melanoma |
| | | Lomustine | Hodgkin's disease, non-Hodgkin's lymphomas, primary brain tumors, small-cell lung |
| | | Semustine | Primary brain tumors, stomach, colon |
| | | Streptozocin | Malignant pancreatic insulinoma, malignant carcinoid |
| | Triazenes | Dacarbazine | Malignant melanoma, Hodgkin's disease, soft-tissue sarcomas |
| | | Procarbazine Aziridine | |
| Antimetabolites | Folic Acid Analogs | Methotrexate Trimetrexate | Acute lymphocytic leukemia, choriocarcinoma, mycosis fungoides, breast, head and neck, lung, osteogenic sarcoma |
| | Pyrimidine Analogs | Fluorouracil Floxuridine | Breast, colon, stomach, pancreas, ovary, head and neck, urinary bladder, premalignant skin lesions (topical) |
| | Purine Analogs and Related Inhibitors | Cytarabine Azacitidine | Acute granulocytic and acute lymphocytic leukemias |
| | | Mercaptopurine | Acute lymphocytic, acute granulocytic, and chronic granulocytic leukemias |
| | | Thioguanine | Acute granulocytic, acute lymphocytic, and chronic granulocytic leukemias |
| | | Pentostatin | Hairy cell leukemia, mycosis fungoides, chronic lymphocytic leukemia |
| | | Fludarabine | Chronic lymphocytic leukemia, Hodgkin's and non-Hodgkin's lymphomas, mycosis fungoides |
| Natural Products | Vinca Alkaloids | Vinblastine (VLB) | Hodgkin's disease, non-Hodgkin's lymphomas, breast, testis |
| | | Vincristine | Acute lymphocytic leukemia, neuroblastoma, Wilms' tumor, rhabdomyosarcoma, Hodgkin's disease, non-Hodgkin's lymphomas, small-cell lung |
| | | Vindesine | Vinca-resistant acute lymphocytic leukemia, chronic myelocytic leukemia, melanoma, lymphomas, breast |
| | Epipodophyl-lotoxins | Etoposide Teniposide | Testis, small-cell lung and other lung, breast, Hodgkin's disease, non-Hodgkin's lymphomas, acute granulocytic leukemia, Kaposi's sarcoma |
| | Antibiotics | Dactinomycin | Choriocarcinoma, Wilms' tumor, rhabdomyosarcoma, testis, Kaposi's sarcoma |
| | | Daunorubicin | Acute granulocytic and acute lymphocytic leukemias |
| | | Doxorubicin 4'-Deoxydoxorubicin | Soft-tissue, osteogenic, and other sarcomas; Hodgkin's disease, non-Hodgkin's lymphomas, acute leukemias, breast, genitourinary, thyroid, lung, stomach, neuroblastoma |
| | | Bleomycin | Testis, head and neck, skin, esophagus, lung, and |

TABLE 2-continued

Chemotherapeutic Agents Useful in Neoplastic Disease[1]

| Class | Type of Agent | Name | Disease[2] |
|---|---|---|---|
| | | | genitourinary tract; Hodgkin's disease, non-Hodgkin's lymphomas |
| | | Plicamycin | Testis, malignant hypercalcemia |
| | | Mitomycin | Stomach, cervix, colon, breast, pancreas, bladder, head and neck |
| | Enzymes | L-Asparaginase | Acute lymphocytic leukemia |
| | Taxanes | Docetaxel Paclitaxel | Breast, ovarian |
| | Biological Response Modifiers | Interferon Alfa | Hairy cell leukemia, Kaposi's sarcoma, melanoma, carcinoid, renal cell, ovary, bladder, non-Hodgkin's lymphomas, mycosis fungoides, multiple myeloma, chronic granulocytic leukemia |
| | | Tumor Necrosis Factor | Investigational |
| | | Tumor-Infiltrating Lymphocytes | Investigational |
| Miscellaneous Agents | Platinum Coordination Complexes | Cisplatin Carboplatin | Testis, ovary, bladder, head and neck, lung, thyroid, cervix, endometrium, neuroblastoma, osteogenic sarcoma |
| | Anthracenedione | Mitoxantrone | Acute granulocytic leukemia, breast |
| | Substituted Urea | Hydroxyurea | Chronic granulocytic leukemia, polycythemia vera, essential thrombocytosis, malignant melanoma |
| | Methyl Hydrazine Derivative | Procarbazine | Hodgkin's disease |
| | Adrenocortical Suppressant | Mitotane Aminoglutethimide | Adrenal cortex Breast |
| Hormones and Antagonists | Adrenocorticosteroids | Prednisone | Acute and chronic lymphocytic leukemias, non-Hodgkin's lymphomas, Hodgkin's disease, breast |
| | Progestins | Hydroxyprogesterone caproate Medroxyprogesterone acetate Megestrol acetate | Endometrium, breast |
| | Estrogens | Diethylstilbestrol Ethinyl estradiol | Breast, prostate |
| | Antiestrogen | Tamoxifen | Breast |
| | Androgens | Testosterone propionate Fluoxymesterone | Breast |
| | Antiandrogen | Flutamide | Prostate |
| | Gonadotropin-releasing hormone analog | Leuprolide Goserelin | Prostate, Estrogen-receptor-positive breast |

[1]Adapted from Calabresi, P., and B. A. Chabner, "Chemotherapy of Neoplastic Diseases" Section XII, pp 1202–1263 in: Goodman and Gilman's The Pharmacological Basis of Therapeutics, Eighth ed., 1990 Pergamin Press, Inc.; and Barrows, L. R., "Antineoplastic and Immunoactive Drugs", Chapter 75, pp 1236–1262, in: Remington: The Science and Practice of Pharmacy, Mack Publishing Co. Easton, PA, 1995.; both references are incorporated by reference herein, in particular for treatment protocols.
[2]Neoplasms are carcinomas unless otherwise indicated.

Even though the invention has been described with a certain degree of particularity, it is evident that many alternatives, modifications, and variations will be apparent to those skilled in the art in light of the foregoing disclosure. Accordingly, it is intended that all such alternatives, modifications, and variations which fall within the spirit and the scope of the invention be embraced by the defined claims.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Cytotoxicity of Bleomycin with Texaphyrin

The present example provides studies on the cytotoxicity of bleomycin with gadolinium texaphyrin as a chemosensitizer. Bleomycin is a basic glycopeptide antibiotic that causes fragmentation of DNA and inhibits incorporation of thymidine into DNA (Barrows, L. R., in Remington: *The Science and Practice of Pharmacy*, Mack Pub. Co., Easton, Pa, 1243–1244, 1995). Gadolinium texaphyrin ("GdT2BET") is compound II, where M=Gd(III).

The in vitro studies were carried out using a modified MTT assay (Mosmann, 1983). MES-SA cells (a hybrid mixed mulleurian human uterine sarcoma cell line, from Stanford School of Medicine, Stanford, Calif.) in McCoy 5A complete medium (0.2 mL containing 3,000–5,000 cells), was pipetted into each well of a 96-well microtiter plate. The cells were allowed to attach overnight. GdT2BET (100 µL; 2 mM in 5% mannitol) was then added to each of the wells at a concentration of 50 µM, 100 µM, or 150 µM. A bleomycin solution (100 µL, 100 µM) was added to each well of the first row of wells on the plate to give a 1:3 dilution of the drug. The medium was mixed thoroughly and 100 µL was transferred to each of the next set of wells for subsequent dilutions. This serial dilution was repeated successively, leaving the last row of wells as controls, discarding the last 100 µL of the drug+texaphyrin/media preparation. These serial transfers resulted in successive dilutions of 1:3, 1:9, 1:27, 1:81, and 1:243 of the original stock bleomycin concentration.

The cells were allowed to grow in the presence of the drug and GdT2BET for 48 hr. MTT [3-(4,5-dimethylthiazol-2-yl)-2,5-diphenyl tetrazolium bromide)] (Sigma, St. Louis, Mo.) (20 µL of 5 mg/mL) in phosphate buffered saline (PBS) was added to each well, and the plate was held in a tissue-culture incubator at 37° C. and under an atmosphere of 5% $CO_2$. After a 2–3 hr incubation, the medium was gently shaken off and replaced with 0.1–0.15 mL isopropanol (JT Baker Chemical Co., Phillipsburg, N.J.) acidified with 0.1N HCl to dissolve formazan crystals formed by the cells. The plate was read at a test wavelength of 570 nm and a reference wavelength of 630 nm on a multiwell spectrophotometer (Model MR580, Dynatech Laboratories, Alexandria, Va.). Each concentration of drug was tested in quadruplicate. Percent survival is defined as percent of the optical density (OD) of the drug-treated cells to that of the control.

The cytotoxicity data of bleomycin at various concentrations in the presence of 50 µM, 100 µM, and 150 µM GdT2BET in MES-SA cells showed that the percent survival of the cells is substantially less in the presence of texaphyrin. This enhancement of cytotoxicity of the bleomycin is seen at all concentrations of bleomycin tested and at all three concentrations of texaphyrin tested.

EXAMPLE 2

Cytotoxicity of Doxorubicin with Texaphyrin

The present example provides studies on the cytotoxicity of doxorubicin (adriamycin) with GdT2BET texaphyrin as a chemosensitizer. Doxorubicin is an anthracycline antibiotic that binds to DNA and inhibits nucleic acid synthesis, inhibits topoisomerase II and produces oxygen radicals; it has the widest antineoplastic spectrum and usefulness of the antineoplastic drugs (Barrows, L. R., in Remington: *The Science and Practice of Pharmacy*, Mack Pub. Co., Easton, Pa., 1249, 1995).

In vitro studies were carried out as described in Example 1 using doxorubicin (100 µL, 1000 nM) and GdT2BET (2 mM in 5% mannitol; at 50 µM, 100 µM, or 150 µM). Results of these studies appear to show a protective effect by the texaphyrin. In vivo results with doxorubicin, provided below, suggest that this in vitro result may be an anomaly due to administering the doxorubicin and the texaphyrin at the same time.

To test this hypothesis, a second in vitro study was carried out as follows. The procedures of Example 1 were followed with the exception that the doxorubicin alone was added to each well of the first row of wells of the microtiter plate and subsequently serially diluted. The drug was allowed to incubate with the cells for 24 hours, after which the wells were washed with media and aspirated off. GdT2BET (at 150 µM conc.) was added to new medium, and the medium was added to each of the wells in the plate. The texaphyrin was allowed to incubate with the cells for 24 hr, after which MTT was added and the study proceeded as described in Example 1. The results of this second in vitro study clearly show an enhancement of cytotoxicity of doxorubicin in the presence of the texaphyrin.

In vivo studies were carried out using Balb/c mice with EMT6 tumors implanted subcutaneously. The EMT6 tumor is a murine mammary sarcoma, and the in vivo antitumor activity of doxorubicin has been previously shown by Grandi et al., (1988) and Di Marco et al., (1972) in MTV mammary carcinoma. In the present studies, adriamycin was dissolved at a concentration of 2 mg/mL in lactated Ringer's solution. GdT2BET was dissolved at a concentration of 2 mM in 5% mannitol. EMT6 tumors (obtained from Dr. J. Martin Brown, Stanford School of Medicine, Stanford, Calif.) were implanted subcutaneously in the right flanks of Balb/c mice (Simonsen Laboratories, Gilroy, Calif.); 14 mice were in each group. The protocol for the study is presented in Table 3.

TABLE 3

Protocol for in vivo Chemosensitization Studies Using Texaphyrins to Enhance the Effect of Doxorubicin (Adriamycin, ADR)

| Group | Adriamycin 7.5 mg/kg, iv | GdT2BET 40 µmol/kg, iv | Additional GdT2BET 40 µmol/kg, iv |
|---|---|---|---|
| control | — | — | — |
| ADR control | yes | — | — |
| 3GdT2BET control | — | yes | 5 & 24 hr post first injection |
| ADR + 1GdT2BET | yes | yes, 5 min post ADR | — |
| ADR + 2GdT2BET | yes | yes, 5 min post ADR | 5 hr post ADR |
| ADR + 3GdT2BET | yes | yes, 5 min post ADR | 5 & 24 hr post ADR |

The protocol was repeated once a week for three weeks; tumors were measured with a vernier caliper 2–3 times a week, and the mice were weighed before the injection.

Results showed a clear enhancement of adriamycin cytotoxicity when an injection of texaphyrin followed the injection of adriamycin in all of the groups. Two cures were observed in the ADR+2GdT2BET group. A "cure" as used herein means that no evidence of disease was found at the end of the study, i.e., the animal appeared to be free of tumor.

A further study was carried out using the abovedescribed ADR control; the abovedescribed ADR+2GdT2BET protocol; and a three-step injection protocol consisting of GdT2BET (40 µmol/kg), followed by ADR (7.5 mg/kg) 5 hr later, followed by GdT2BET (40 µmol/kg) 5 min after the ADR injection. This protocol was repeated once a week for three weeks, and the tumors were measured by vernier caliper 2–3 times a week. Results showed enhanced cytotoxicity in the presence of gadolinium texaphyrin, including the observation of two cures in the ADR+2GdT2BET group. The data further suggest that the three-step regimen of texaphyrin/ADR/texaphyrin may be too cytotoxic since three deaths out of six animals were observed in this group, two after the first texaphyrin injection and one after the last texaphyrin injection.

A standard error analysis of the data obtained from injecting adriamycin only (ADR) and injecting adriamycin followed by texaphyrin 5 min and 5 hr later (ADR+ 2GdT2BET) is provided in FIG. 1. Four cures were observed in the ADR+2GdT2BET group, with a $p<0.05$ after day 9.

Data presented in this example provide a clear showing of chemosensitization by texaphyrin due to the enhanced cytotoxicity of doxorubicin when administered in an appropriate regimen with texaphyrin.

EXAMPLE 3

Cytotoxicity of Paclitaxel with Texaphyrin

The present example provides studies on the cytotoxicity of paclitaxel with gadolinium texaphyrin as a chemosensitizer. Paclitaxel (Bristol-Myers Oncology name for Taxol) inhibits mitosis by stabilizing mitotic spindles and inappropriately promoting their formation (Barrows, L. R., in Remington: *The Science and Practice of Pharmacy*, Mack Pub. Co., Easton, Pa., 1249, 1995).

In vitro studies were carried out as described in Example 1 with paclitaxel (100 µL, 1000 nM), and GdT2BET (50 µM, 100 µM, or 150 µM) added to each dilution of the drug. Results of these studies show an enhancement of cytotoxicity, especially at lower concentrations of paclitaxel.

EXAMPLE 4

Cytotoxicity of 4-OH Cyclophosphamide with Texaphyrin

The present example provides studies on the cytotoxicity of 4-OH cyclophosphamide with gadolinium texaphyrin as a chemosensitizer. Cyclophosphamide is an alkylating agent (Barrows, L. R., in Remington: *The Science and Practice of Pharmacy*, Mack Pub. Co., Easton, Pa., 1249, 1995).

In vitro studies were carried out as described in Example 1 with 4-OH cyclophosphamide (100 µL, 100 µM), and GdT2BET (50 µM, 100 µM, and 150 µM) added to each dilution of the drug. Results of these studies appear to show a protective effect at lower concentrations of 4-OH cyclophosphamide. This in vitro result may be an anomaly, similar to the anomalous result seen in Example 2 with doxorubicin due to administering the drug and the texaphyrin at the same time.

In vivo studies were carried out using Balb/c mice with EMT6 tumors implanted subcutaneously as described in Example 2. 4-Hydroxy cyclophosphamide was dissolved at a concentration of 5 mg/mL in 0.9% NaCl. GdT2BET was dissolved at a concentration of 2 mM in 5% mannitol. EMT6 tumors were implanted subcutaneously in the right flanks of Balb/c mice; 9 mice were in each group. Group #1 received cyclophosphamide (CY) at 40 mg/kg; group #2 received cyclophosphamide (CY) at 40 mg/kg followed by GdT2BET at 40 µmol/kg 5 min later; and group #3 received cyclophosphamide (CY) at 40 mg/kg followed by GdT2BET at 40 µmol/kg 5 min and 5 hr later. This protocol was repeated once a week for three weeks.

Results appear to suggest that little chemosensitization occurred under this particular regimen of treatment using texaphyrin and cyclophosphamide. Results demonstrated in Example 2 with doxorubicin suggest that the texaphyrin chemosensitization effect may be somewhat regimen-dependent, and further studies would clarify whether cyclophosphamide cytotoxicity could be enhanced by texaphyrin under other regimens.

EXAMPLE 5

Cytotoxicity of Etoposide with Texaphyrin

The present example provides studies on the cytotoxicity of etoposide with gadolinium texaphyrin as a chemosensitizer. Etoposide damages DNA, most likely via topoisomerase II cleavage, and arrests the cell cycle primarily in phase G2 (Barrows, L. R., in Remington: *The Science and Practice of Pharmacy*, Mack Pub. Co., Easton, Pa., 1249, 1995).

In vitro studies were carried out as described in Example 1 with etoposide (100 µL, 100 µM), and GdT2BET (50 µM, 100 µM, or 150 µM) added to each dilution of the drug. Results of these studies show an enhancement of cytotoxicity, especially at lower concentrations of etoposide.

EXAMPLE 6

Cytotoxicity of Cisplatin with Texaphyrin

The present example provides studies on the cytotoxicity of cisplatin with gadolinium texaphyrin as a chemosensitizer. Cisplatin cross-links DNA and therefore acts like an alkylating antineoplastic agent (Barrows, L. R., in Remington: *The Science and Practice of Pharmacy*, Mack Pub. Co., Easton, Pa., 1249, 1995).

In vitro studies were carried out as described in Example 1 with cisplatin (100 µL, 100 µM), and GdT2BET (50 µM, 100 µM, and 150 µM) added to each dilution of the drug. Results of these studies show an enhancement of cytotoxicity, especially at lower concentrations of cisplatin.

EXAMPLE 7

Summary of In Vitro Texaphyrin Chemosensitization Results

Figure 2:
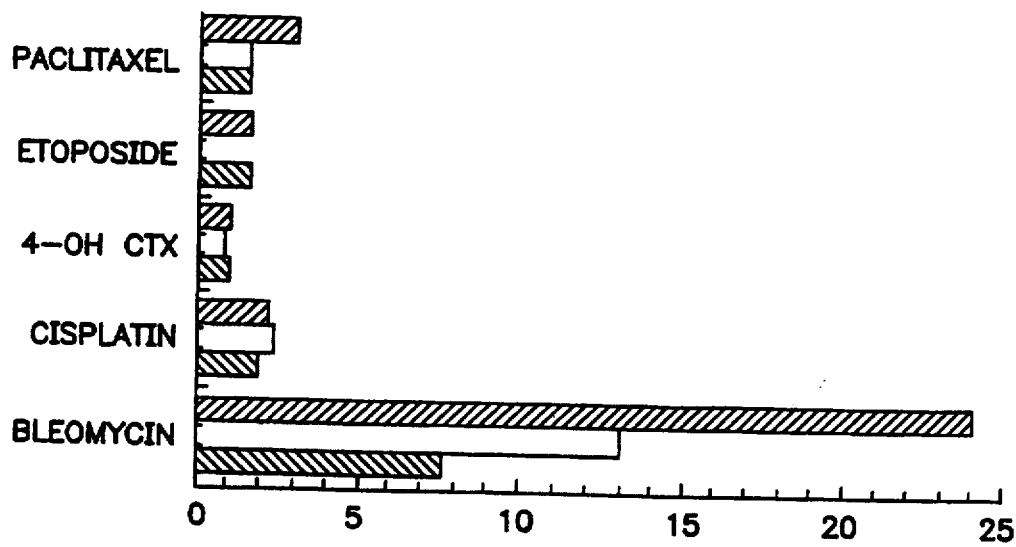
FIG. 2 demonstrates the $IC_{50}$ difference relative to control with three different concentrations of texaphyrin (\\\\\+50 µM, □+100 µM, //// +150 µM), and a chemotherapeutic agent in MES-SA cells. The agents tested with texaphyrin were paclitaxel, etoposide, 4-OH cyclophosphamide, cisplatin and bleomycin.

The present example provides a summary of results obtained from the in vitro MTT cytotoxicity assays provided in Examples 1, and 3–6. FIG. 2 demonstrates the $IC_{50}$ difference relative to control with three different concentrations of GdT2BET and a chemotherapeutic agent in MES-SA cells. The agents tested with texaphyrin were paclitaxel, etoposide, 4-OH cyclophosphamide, cisplatin and bleomycin. Data from studies with doxorubicin are not included in this summary since that in vitro regimen differed somewhat as described in Example 2. All agents demonstrated enhanced cytotoxicity in the presence of texaphyrin, and bleomycin demonstrated a particularly dramatic enhancement of activity (FIG. 2).

EXAMPLE 8

Hematology Study for Texaphyrin and Doxorubicin

The present example provides a summary of results obtained from a hematology study carried out on normal mice to test for any combined toxicity from gadolinium texaphyrin and doxorubicin.

A control group of eight Balb/c mice received no treatment. A second group of eight received injections of doxorubicin at 7.5 mg/kg/week for three weeks. A third group received injections of doxorubicin as group #2, followed 5 min later by GdT2BET at 40 μmol/kg/week for three weeks. Normal values were obtained from the California Veterinary Diagnostics, Inc. (West Sacramento, Calif.). White blood cell counts, red blood cell counts, hemoglobin values in gm/dL and platelet counts were obtained two weeks after the first injection and two weeks after the last injection.

Results clearly show no enhanced doxorubicin-induced bone marrow toxicity when the texaphyrin was used with doxorubicin, as measured by peripheral white blood cell count, platelet count and hemoglobin. In all four parameters studied, and in both time frames, values for the group of mice receiving doxorubicin and texaphyrin were very close to and within the error values found for the group of mice receiving doxorubicin only. These results emphasize the nontoxicity of texaphyrins in vivo, especially a lack of toxicity on bone marrow.

EXAMPLE 9

Texaphyrin Uptake and Chemosensitization Effect

In an MDR and a non-MDR Cell Line

The present example provides data that indicate the uptake of lutetium texaphyrin and the chemosensitization effect of gadolinium texaphyrin are independent of the multidrug resistance phenotype of the host.

A murine leukemia cell line expressing the multidrug resistance protein, P388/ADR (Gottesman and Pastan, 1993), and a cell line lacking this protein, P388 (Johnson et al., 1982) were tested for uptake of lutetium texaphyrin. P388 and P388/ADR cells were suspended in FHS medium at a cell density of 7 mg/ml wet weight (Fisher's medium with 20 mM HEPES, pH 7.2, replacing NaHCO$_3$), and incubated with lutetium texaphyrin (compound II where M=Lu(III); "LuT2BET") for 30 min at 37° C. Fluorescence measurements demonstrated no difference in texaphyrin uptake between the two cell lines.

A wild-type human sarcoma cell line, MES-SA, and a doxorubicin-selected mdr1 variant, MES-SA/Dx5 (Stanford School of Medicine, Stanford, Calif.) were tested with the chemotherapeutic agents 4-OH cyclophosphamide, etoposide, doxorubicin, cisplatin, and bleomycin in the presence of GdT2BET. All chemotherapeutic agents were effective in the presence of texaphyrin in both cell lines, suggesting that the mechanism of action is P-glycoprotein-independent.

EXAMPLE 10

Method for Selecting Chemotherapeutic Agents For Which Texaphyrin is a Chemosensitizer The present example provides methods for selecting chemotherapeutic agents for which texaphyrin is a chemosensitizer. Candidate chemotherapeutic agents are screened for enhanced activity in the presence of texaphyrin using an in vitro cytotoxicity assay such as the MTT cytotoxicity test described in Example 1. Additionally, or alternatively, candidate chemotherapeutic agents are evaluated in in vivo models for enhanced activity in the presence of texaphyrin. An example is the mouse study described in Example 2. A chemotherapeutic agent having increased cytotoxicity in the presence of texaphyrin compared to the level of cytotoxicity in the absence of texaphyrin is considered a chemotherapeutic agent for which texaphyrin is a chemosensitizer.

Further, a transgenic mouse was developed for testing agents as potential chemosensitizers in reversing drug resistance (Mickisch, et al., 1991). The mice express the MDR gene in their bone marrow cells and are resistant to leukopenia induced by natural products such as anthracyclines. This drug resistance may be circumvented in a dose-dependent manner by simultaneous administration of agents such as verapamil and quinine. This MDR1-transgenic mouse model may also be used to test for those chemotherapeutic agents for which texaphyrin is a chemosensitizer.

The dose, schedule, and method of administration of the chemotherapeutic agent and the texaphyrin is varied to optimize the chemosensitization effect. The timing and method of administration of each agent, the dosage of each agent, the circadian rhythm response of the animal to each agent, are factors to be varied one at a time for optimization of chemosensitization by texaphyrins.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Barrows, L. R., "Antineoplastic and Immunoactive Drugs", Chapter 75, pp 1236–1262, in: *Remington: The Science and Practice of Pharmacy*, Mack Publishing Co. Easton, Pa., 1995.

Dalton, W. S., *Proc. Am. Assoc. Cancer Res.* 31:520, 1990.

DeVita, V. T., et al., in *Cancer, Principles & Practice of Oncology*, 4th ed., J. B. Lippincott Co., Philadelphia, Pa., pp 2661–2664, 1993.

Di Marco, A., et al., *Cancer Chemotherapy Reports*, 56:153–161, 1972.

Calabresi, P., and B. A. Chabner, "Chemotherapy of Neoplastic Diseases" Section XII, pp 1202–1263 in: *Goodman and Gilman's The Pharmacological Basis of Therapeutics*, Eighth ed., 1990 Pergamin Press, Inc.

Gottesman, M. M., and I. Pastan, *Ann. Rev. Biochem.*, 62:385–427, 1993.

Grandi, M., et al., "Screening of anthracycline analogs." In *Anthracycline and anthracenedione-based anticancer agents. Bioactive molecules.* Vol. 6, Chapter XV. ed. JW Lown, Elsevier, 1988.

Johnson, R. K., et al., *Cancer Treat. Rep.* 62:1535–1547, 1982.

Mickisch, G. H., et al., *Proc. Natl. Acad. Sci. USA*, 88:547–551, 1991.

Mosmann, J. *Immunological Methods*, 65:55–63, 1983.

Raderer, M., and Scheithauer, W., *Cancer*, 72(12):3553–3563, 1993.

What is claimed is:

1. A method of chemosensitization comprising administering a chemotherapeutic agent and a texaphyrin to a subject in need thereof.

2. A method of treating cancer in a subject in need of treatment comprising
    administering a chemotherapeutic agent and a texaphyrin to the subject.

3. A method of treating cancer in a subject in need of treatment comprising:
    administering a chemotherapeutic agent and a photosensitive texaphyrin to the subject, and
    irradiating the subject in the vicinity of the cancer.

4. A method of treating cancer in a subject in need of treatment comprising:
    administering a chemotherapeutic agent and a texaphyrin having radiosensitization properties to the subject, and
    administering ionizing radiation to the subject in proximity to the cancer.

5. A method of chemosensitization comprising administering a chemotherapeutic agent and a texaphyrin having structure I to a subject in need thereof:

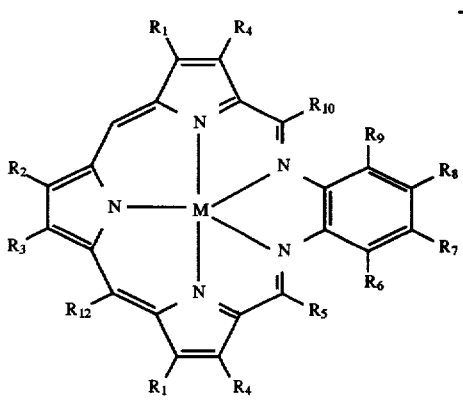

wherein

M is a divalent metal cation, or a trivalent metal cation;

$R_1$–$R_4$, $R_7$ and $R_8$ are independently hydrogen, halide, hydroxyl, alkyl, aryl, haloalkyl, nitro, formyl, acyl, hydroxyalkyl, alkoxy, hydroxyalkoxy, saccharide, carboxy, carboxyalkyl, carboxyamidealkyl, a site-directing molecule, or a couple that is coupled to a site-directing molecule;

$R_6$ and $R_9$ are independently selected from the groups of $R_1$–$R_4$, R7 and $R_8$, with the proviso that the halide is other than iodide and the haloalkyl is other than iodoalkyl;

$R_5$ and $R_{10}$–$R_{12}$ are independently hydrogen, alkyl, aryl, hydroxyalkyl, alkoxy, hydroxyalkoxy, carboxyalkyl, carboxyamidealkyl or a couple that is coupled to a saccharide or to a site-directing molecule; and n is an integer less than or equal to 5.

6. A method of treating cancer in a subject in need of treatment comprising administering a chemotherapeutic agent and a texaphyrin having structure I to the subject:

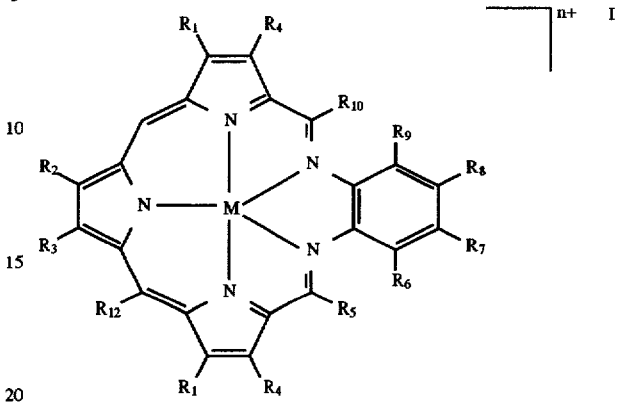

wherein

M is a divalent metal cation, or a trivalent metal cation;

$R_1$–$R_4$, $R_7$ and $R_8$ are independently hydrogen, halide, hydroxyl, alkyl, aryl, haloalkyl, nitro, formyl, acyl, hydroxyalkyl, alkoxy, hydroxyalkoxy, saccharide, carboxy, carboxyalkyl, carboxyamidealkyl, a site-directing molecule, or a couple that is coupled to a site-directing molecule;

$R_6$ and $R_9$ are independently selected from the groups of $R_1$–$R_4$, $R_7$ and $R_8$, with the proviso that the halide is other than iodide and the haloalkyl is other than iodoalkyl;

$R_5$ and $R_{10}$–$R_{12}$ are independently hydrogen, alkyl, aryl, hydroxyalkyl, alkoxy, hydroxyalkoxy, carboxyalkyl, carboxyamidealkyl or a couple that is coupled to a saccharide or to a site-directing molecule; and n is an integer less than or equal to 5.

7. A method of treating cancer in a subject in need of treatment comprising:
    administering a chemotherapeutic agent and a photosensitive texaphyrin having structure I to the subject, and
    irradiating the subject in the vicinity of the cancer:

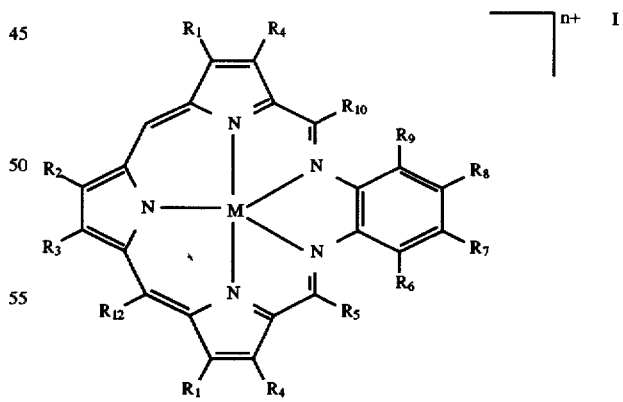

wherein

M is a diamagnetic metal cation;

$R_1$–$R_4$, $R_7$ and $R_8$ are independently hydrogen, halide, hydroxyl, alkyl, aryl, haloalkyl, nitro, formyl, acyl, hydroxyalkyl, alkoxy, hydroxyalkoxy, saccharide, carboxy, carboxyalkyl, carboxyamidealkyl, a site-directing molecule, or a couple that is coupled to a site-directing molecule;

$R_6$ and $R_9$ are independently selected from the groups of $R_1$–$R_4$, $R_7$ and $R_8$, with the proviso that the halide is other than iodide and the haloalkyl is other than iodoalkyl;

$R_5$ and $R_{10}$–$R_{12}$ are independently hydrogen, alkyl, aryl, hydroxyalkyl, alkoxy, hydroxyalkoxy, carboxyalkyl, carboxyamidealkyl or a couple that is coupled to a saccharide or to a site-directing molecule; and n is an integer less than or equal to 5.

8. A method of treating cancer in a subject in need of treatment comprising:

administering a chemotherapeutic agent and a texaphyrin having radiosensitization properties and having structure I to the subject, and administering ionizing radiation to the subject in proximity to the cancer:

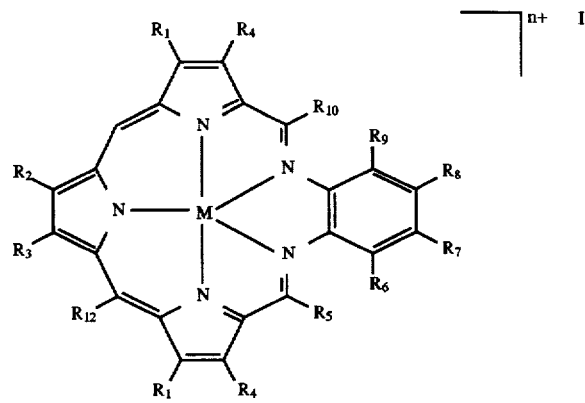

wherein

M is a divalent metal cation, or a trivalent metal cation;

$R_1$–$R_4$, $R_7$ and $R_8$ are independently hydrogen, halide, hydroxyl, alkyl, aryl, haloalkyl, nitro, formyl, acyl, hydroxyalkyl, alkoxy, hydroxyalkoxy, saccharide, carboxy, carboxyalkyl, carboxyamidealkyl, a site-directing molecule, or a couple that is coupled to a site-directing molecule;

$R_6$ and $R_9$ are independently selected from the groups of $R_1$–$R_4$, $R_7$ and $R_8$, with the proviso that the halide is other than iodide and the haloalkyl is other than iodoalkyl;

$R_5$ and $R_{10}$–$R_{12}$ are independently hydrogen, alkyl, aryl, hydroxyalkyl, alkoxy, hydroxyalkoxy, carboxyalkyl, carboxyamidealkyl or a couple that is coupled to a saccharide or to a site-directing molecule; and n is an integer less than or equal to 5.

9. The method of claim 1, 2, 3, or 4 wherein the texaphyrin has an alkyl group attached to a ring nitrogen.

10. The method of claim 1, 2, or 4 wherein the texaphyrin is a photosensitive texaphyrin.

11. The method of claim 10 where the photosensitive texaphyrin is complexed with a diamagnetic metal cation and the diamagnetic metal cation is Lu(III), La(III), In(III), Y(III), Zn(II) or Cd(II).

12. The method of claim 11 where the diamagnetic metal cation is Lu(III).

13. The method of claim 1, 2, or 4 wherein the texaphyrin is complexed with a paramagnetic metal cation and the method further comprises the step of imaging the subject.

14. The method of claim 13 wherein the paramagnetic metal cation is Mn(II), Mn(III), Fe(III), or a trivalent lanthanide metal cation other than La(III), Lu(III), and Pm(III).

15. The method of claim 13 wherein the paramagnetic metal cation is Mn(II), Mn(III), Dy(III), or Gd(III).

16. The method of claim 13 wherein the paramagnetic metal cation is Gd(III).

17. The method of claim 5, 6, or 8 wherein M is a trivalent metal cation, and the trivalent metal cation is Lu(III) or Gd(III).

18. The method of claim 7 wherein the diamagnetic metal cation is Lu(III), La(III), In(III), Y(III), Zn(II) or Cd(II).

19. The method of claim 5, 6, 7, or 8 wherein $R_1$ is $CH_2(CH_2)_2OH$, $R_2$ and $R_3$ are $CH_2CH_3$, $R_4$ is $CH_3$, $R_7$ and $R_8$ are $O(CH_2CH_2O)_3CH_3$, and $R_5$, $R_6$, and $R_9$–$R_{12}$ are H.

20. The method of claim 1, 2, 3, 4, 5, 6, 7, or 8 wherein the chemotherapeutic agent is an alkylating agent, an antimetabolite, a natural product, a hormone or an antagonist.

21. The method of claim 1, 2, 3, 4, 5, 6, 7, or 8 wherein the chemotherapeutic agent is a platinum coordination complex, an anthracenedione, an anthracycline, a substituted urea, a methyl hydrazine derivative, or an adrenocortical suppressant.

22. The method of claim 1, 2, 3, 4, 5, 6, 7, or 8 wherein the chemotherapeutic agent is paclitaxel, etoposide, 4-OH cyclophosphamide, cisplatin, doxorubicin, or bleomycin.

23. The method of claim 1, 2, 3, 4, 5, 6, 7, or 8 wherein the chemotherapeutic agent is doxorubicin or bleomycin.

24. The method of claim 1, 2, 3, 4, 5, 6, 7, or 8 wherein the texaphyrin is administered after administration of the chemotherapeutic agent.

25. The method of claim 1, 2, 3, 4, 5, 6, 7, or 8 wherein the administering of the texaphyrin is topical.

26. The method of claim 1, 2, 3, 4, 5, 6, 7, or 8 wherein the administering of the texaphyrin is intravenous.

27. The method of claim 1, 2, 3, 4, 5, 6, 7, or 8 wherein the texaphyrin acts as a chemosensitizer in a P-glycoprotein-independent mechanism.

28. The method of claim 2, 3, 4, 6, 7, or 8 wherein the cancer is leukemia, lymphoma, carcinoma, or sarcoma.

29. The method of claim 3 wherein the irradiating is at a wavelength of about 700–900 nm.

30. The method of claim 3 further comprising the steps of administering a texaphyrin complexed with a paramagnetic metal cation to the subject, and imaging the subject.

31. The method of claim 4 wherein the ionizing radiation is from an x-ray, a gamma-emitting radioisotope, or an ionizing particle.

32. The method of claim 1 or 2 wherein the chemotherapeutic agent is selected from the group consisting of doxorubicin and bleomycin, and the texaphyrin is GdT2BET.

33. The method of claim 5 or 6 wherein the chemotherapeutic agent is selected from the group consisting of doxorubicin and bleomycin; $R_1$ is $CH_2(CH_2)_2OH$, $R_2$ and $R_3$ are $CH_2CH_3$, $R_4$ is $CH_3$, $R_7$ and $R_8$ are $O(CH_2CH_2O)_3CH_3$, and $R_5$, $R_6$, and $R_9$–$R_{12}$ are H; and M is Gd(III).

34. The method of claim 1, 2, 5, or 6 wherein the texaphyrin is selected from the group of texaphyrins consisting of A1–A22 of Table 1.

* * * * *

UNITED STATES PATENT AND TRADEMARK OFFICE
CERTIFICATE OF CORRECTION

PATENT NO. : 5,776,925
DATED : July 7, 1998
INVENTOR(S) : Young, et. al.

It is certified that error appears in the above-identified patent and that said Letters Patent is hereby corrected as shown below:

In Claim 5, column 25, lines 35-50; in Claim 6, column 26, lines 5-20; in Claim 7, column 26, lines 44-59; and in Claim 8, column 27, lines 17-32; delete "

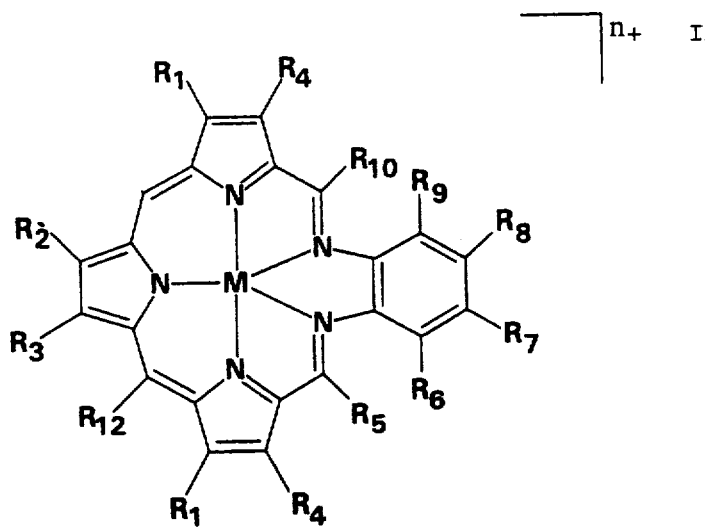

and substitute – –

UNITED STATES PATENT AND TRADEMARK OFFICE
CERTIFICATE OF CORRECTION

PATENT NO. : 5,776,925
DATED : July 7, 1998
INVENTOR(S) : Young, et. al.

Page 2 of 2

It is certified that error appears in the above-identified patent and that said Letters Patent is hereby corrected as shown below:

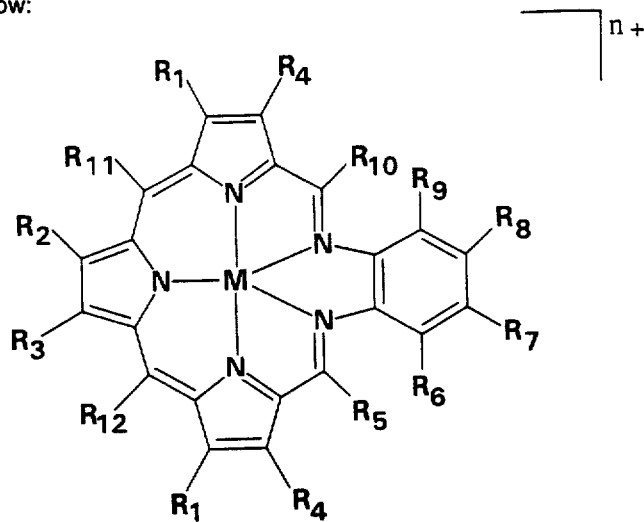

I

--, therefor.

Signed and Sealed this

Twenty-second Day of September, 1998

Attest:

BRUCE LEHMAN

Attesting Officer

Commissioner of Patents and Trademarks